United States Patent [19]

Hitzeman et al.

[11] Patent Number: 5,919,651
[45] Date of Patent: Jul. 6, 1999

[54] EXPRESSION OF POLYPEPTIDES IN YEAST

[75] Inventors: Ronald A. Hitzeman, Pacifica; Franklin E. Hagie, IV, Foster City, both of Calif.; Benjamin D. Hall, Bellevue; Gustav Ammerer, Seattle, both of Wash.

[73] Assignees: Washington Research Foundation, Seattle, Wash.; Genentech, Inc., South San Francisco, Calif.

[*] Notice: This patent is subject to a terminal disclaimer.

[21] Appl. No.: 08/465,927

[22] Filed: Jun. 6, 1995

Related U.S. Application Data

[63] Continuation of application No. 08/383,668, Feb. 3, 1995, abandoned, which is a continuation of application No. 08/198,535, Feb. 18, 1994, abandoned, which is a continuation of application No. 08/089,419, Jul. 9, 1993, abandoned, which is a continuation of application No. 07/708,828, May 29, 1991, abandoned, which is a continuation of application No. 07/349,918, May 9, 1989, abandoned, which is a continuation of application No. 07/284,774, Dec. 12, 1988, abandoned, which is a continuation of application No. 07/173,008, Mar. 28, 1988, abandoned, which is a continuation of application No. 06/764,145, Aug. 9, 1985, abandoned, which is a continuation of application No. 06/237,913, Feb. 25, 1981, abandoned.

[51] Int. Cl.⁶ ................................................. C12P 21/00
[52] U.S. Cl. ................. 435/69.1; 435/254.2; 435/320.1; 435/483; 435/254.21
[58] Field of Search ........................... 435/254.2, 254.21, 435/69.1–69.9, 320.1, 172.3, 942, 91.1, 255.1, 255.2, 254.1, 483; 935/28, 37, 60, 67; 536/23.5, 23.51, 23.52, 24.1, 23.1

[56] References Cited

U.S. PATENT DOCUMENTS

| | | | |
|---|---|---|---|
| 4,237,224 | 12/1980 | Cohen et al. | 435/69.1 |
| 4,349,629 | 9/1982 | Carey et al. | 435/172.3 |
| 4,356,270 | 10/1982 | Itakura et al. | 435/320.1 |
| 4,366,246 | 12/1982 | Riggs | 435/69.8 |
| 4,387,162 | 6/1983 | Aigie et al. | 435/254.21 |
| 4,425,437 | 1/1984 | Riggs | 435/320.1 |
| 4,428,941 | 1/1984 | Galibert et al. | 514/2 |
| 4,431,739 | 2/1984 | Riggs | 435/252.33 |
| 4,563,424 | 1/1986 | Riggs | 435/69.4 |
| 4,615,974 | 10/1986 | Kingsman et al. | 435/69.51 |
| 4,634,677 | 1/1987 | Goeddel et al. | 435/320.1 |
| 4,658,021 | 4/1987 | Goeddel et al. | 530/399 |
| 4,666,847 | 5/1987 | Alford et al. | 435/252.33 |
| 4,769,238 | 9/1988 | Rutter et al. | 435/69.3 |

FOREIGN PATENT DOCUMENTS

| | | |
|---|---|---|
| 0001929 | 5/1979 | European Pat. Off. . |
| 0013828 | 3/1981 | European Pat. Off. . |
| 35454 | 9/1981 | European Pat. Off. . |
| 43980 | 1/1982 | European Pat. Off. . |
| 48970 | 4/1982 | European Pat. Off. . |
| 55945 | 4/1982 | European Pat. Off. . |
| 0072670 | 4/1983 | European Pat. Off. . |
| 2458585 | 1/1981 | France . |
| 2008123 | 5/1979 | United Kingdom . |
| 2068969 | 8/1981 | United Kingdom . |
| WO81/02425 | 9/1981 | WIPO . |

OTHER PUBLICATIONS

Beggs, J.D., "Transformation of yeast by a replicating hybrid plasmid," *Nature* 275:104–109 (1978).

Beggs, J.D., et al., "Abnormal expression of chromosomal rabbit β–globin gene in *Saccharomyces cerevisiae*," *Nature* 283:835–840 (Feb. 28, 1980).

Broach, J.R., et al., "Transformation in yeast: Development of a hybrid cloning vector and isolation of the CAN1 gene," *Gene* 8:121–133, (1979).

Broach, J.R., et al., "Identification and mapping of the transcriptional and translational products of the yeast plasmid, 2μcircle," *Cell* 16:827–839 (1979).

Broach, J.R., and J.B. Hicks, "Replication and recombination functions associated with the yeast plasmid, 2μ circle," *Cell* 21:501–508 (Sep. 1980).

Carbon, J., et al., "The isolation and characterization of specific gene systems from the yeast *Saccharomyces cerevisiae*," in *Biochemistry and Genetics of Yeasts*, N. Bacila, et al., (Eds.), Academic Press, pp. 425–443 (1978).

Chakrabarty, A.M., ed., "Genetic Engineering," pp. 17–18 (1978).

Chevallier, M.R., et al., "Qualitative detection of penicillinase produced by yeast strains carrying chimeric yeast–coli plasmids," *Chem. Abstr.* 92:54695y (1980).

Clarke, L., and J. Carbon, "Biochemical construction and selection of hybrid plasmids containing specific segments of the *Escherichia coli* genome," *Proc. Nat. Acad. Sci. USA* 72(11):4361–4365 (1975).

Clark, L., and J. Carbon, "Isolation of a yeast centromere and construction of functional small circular chromosomes," *Nature* 287:504–509 (Oct. 9, 1980).

Clarke, L., and J. Carbon, "Isolation of the centromere–linked CDC10 gene by complementation in yeast," *Proc. Nat. Acad. Sci. USA* 77(4):2173–2177 (Apr. 1980).

Cohen, J.D., et al., "Functional expression in yeast of the *Escherichia coli* plasmid gene coding for chloramphenicol acetyltransferase," *Proc. Nat. Acad. Sci. USA* 77(2):1078–1082 (Feb. 1980).

Davis, R.W., et al., "Rapid DNA isolations for enzymatic and hybridization analysis," *Methods in Enzymology* 65:404–411 (1980).

DeMoss, J.A., "Biochemical diversity of the tryptophan pathway," *Biochem. Biophys. Res. Commun.* 18(5–6):850–857 (1965).

(List continued on next page.)

*Primary Examiner*—James Martinell
*Attorney, Agent, or Firm*—Christensen O'Connor Johnson & Kindness PLLC

[57] ABSTRACT

DNA expression vectors capable, in a transformant strain of yeast, of expressing a polypeptide under the control of a genetically distinct yeast promoter, processes of forming transformant strains of yeast and transformed yeast strains are disclosed.

38 Claims, 5 Drawing Sheets

OTHER PUBLICATIONS

Derynck, R., et al., "Expression of human fibroblast interferon gene in *Escherichia coli*," *Nature* 287:193–197 (Sep. 1980).

Fraser, T.H., and B.J. Bruce, "Chicken ovalbumin is synthesized and secreted by *Escherichia coli*," *Proc. Nat. Acad. Sci. USA* 75(12):5936–5490 (1978).

Fraser, T.H., and B.J. Bruce, "Synthesis of chicken ovalbumin in *Saccharomyces cerevisiae*," in *Microbiology–1981*, D. Schlessinger, Ed., American Society for Microbiology, Washington, D.C., pp. 392–395 (1981).

Goeddel, D.V., et al., "Human leukocyte interferon produced by *E. coli* is biologically active," *Nature* 287:411–416 (1980).

Hall, et al., "Transcription initiation of eukaryote transfer RNA genes," *Cell* 29:3–5 (1982).

Hartley, J.L., and J.E. Donelson, "Nucleotide sequence of the yeast plasmid," *Nature* 286:860–864 (Aug. 1980).

Henikoff, S., et al., "Isolation of a gene from Drosophila by complementation in yeast," *Nature* 289:33–37 (Jan. 1981).

Hinnen, A., et al., "Transformation of yeast," *Proc. Nat. Acad. Sci. USA* 75(4):1929–1933 (1978).

Hitzeman, R.A., et al., "Isoloation and characterization of the yeast 3–phosphoglycerokinase gene (PGK) by an immunological screening technique," *The Journal of Biological Chemistry* 255:12073–12080 (1980).

Hitzeman, R.A., et al., "Expression of a human gene for interferon in yeast," *Nature* 293(5835):717–722 (Oct. 29, 1981).

Hitzeman, R.A, et al., "Expression, processing and secretion of heterologous gene products by yeast," *Rec. Adv. Yeast Mol. Biol.* 1:173–190 (1982).

Hitzeman, R.A., et al., "Expression of hepatitis B virus surface antigen in yeast," *Nucleic Acids Research* 11(9):2745–2763 (1983).

Holland, J.P., and M.J. Holland, "The primary structure of a glyceraldehyde–3–phosphate dyhydrogenase gene from *Saccharomyces cerevisiae*," *The Journal of Biological Chemistry* 254(19):9839–9845 (1979).

Holland, J.P. and M.J. Holland, "Structural comparison of two nontandemly repeated yeast glyceraldehyde–3–phosphate dehydrogenase genes," *The Journal of Biological Chemistry* 255(6):2596–2605 (1980).

Hsiao, C.–L., et al., "High frequency transformation of yeast by plasmids containing the cloned yeast ARG4 gene," *Proc. Nat. Acad. Sci. USA* 76(8):3829–3833, 1979.

Ilgen, C., et al., "Transformation of yeast," in *Genetic Engineering: Principles and Methods*, vol. 1, J.K. Setlow and A. Hollaender, Eds., Plenum Press, N.Y., pp. 117–132 (1979).

Itakura, K., et al., "Expression in *Escherichia coli* of a chemically synthesized gene for the hormone somatostatin," *Science* 198:1056–1063 (1977).

Kingsman, A.J., et al., "Replication in *Saccharomyces cerevisiae* of plasmid pBR313 carrying DNA from the yeast trp1 region," *Gene* 7:141–153 (1979).

Koski, R.A., et al., "An in vitro RNA polymerase III system from *S. cerevisiae*: effects of deletions and point mutations upon SUP4 gene transcription," *Nucleic Acids Research* 10(24):8127–8143 (1982).

Kramer, R.A., et al., "Regulated expression of a human interferon gene in yeast: control by phosphate concentration or temperature," *Proc. Nat. Acad. Sci. USA* 81:367–370 (1984).

Maniatis, T., "Recombinant DNA procedures in the study of eukaryotic genes," *Cell Biology* 3:594 (1980).

Maxam, A.M., et al., "Promoter region for yeast 5S ribosomal RNA," *Nature* 267:643–645 (1977).

Mercereau–Puijalon, O., et al., "Synthesis of a chicken ovalbumen–like protein in the yeast *Saccharomyces cerevisiae*," *Gene* 11:163–167 (1980).

Miyanohara, A., et al., "Expression of hepatitis B surface antigen in yeast," *Proc. Nat. Acad. Sci. USA* 80:1–5 (1983).

Newmark, P., "Benefits and snags of yeast plasmids," *Nature* 290:77 (Mar. 1981).

Oliver, S.G., et al., *Dictionary of Genetic Engineering*, Cambridge University Press, London (1985).

Panthier, J.–J., et al., "Génie Génétique–Sur l'expression d'un géne bactérien cloné dans la levure *Saccharomyces cerevisiae*," C.R. Acad Sc. Paris 289(Série D):773–775 (1979).

Panthier, J.–J., et al., "Cloned β–galactosidase gene of *Escherichia coli* is expressed in the yeast *Saccharomyces cerevisiae*," *Current Genetics* 2:109–113 (1980).

Ratzkin, B., and J. Carbon, "Functional expression of cloned yeast DNA in *Esherichia coli*," *Proc. Nat. Acad. Sci. USA* 74(2):487–491 (1977).

Sakonju, S., et al., "A control region in the center of the 5S RNA gene directs specific initiation of transcription: I. The 5' border of the region," *Cell* 19:13–25 (1980).

Stinchcomb, D.T., et al., "Isolation and characterization of a yeast chromosomal replicator," *Nature* 282:39–43, 1979.

Struhl, K., et al., "High–frequency transformation of yeast: Atonomous replication of hybrid DNA molecules," *Proc. Nat. Acad. Sci. USA* 76(3):1035–1039 (1979).

Tschumper, G., and J. Carbon, "Sequence of a yeast DNA fragment containing a chromosomal replicator and the TRP1 gene," *Gene* 10:157–166 (1980).

Tuite, M.F., et al., "Regulated high efficiency expression of human interferon–alpha in *Saccharomyces cerevisiae*," in *The EMBO Journal* 1(5):603–608 (1982).

Urdea, M.S., et al., "Chemical synthesis of a gene for human epidermal growth factor urogastrone and its expression in yeast," *Proc. Nat. Acad. Sci. USA* 80:7461–7465 (1983).

Walz, A., et al., "Control of expression of a cloned yeast (*Saccharomyces cerevisiae*) gene (trp5) by a bacterial insertion element (IS2)," *Proc. Nat. Acad. Sci. USA* 75:6172–6176 (1978).

Williamson, V.M., et al., "Isolation of the structural gene for alcohol dehydrogenase by genetic complementation in yeast," *Nature* 283:214–216 (Jan. 1980).

Ammerer, et al., "The functional expression of mammalian genes in yeast, in Recombinant DNA," *Proceedings of the Third Cleveland Symposium on Macromolecules*, Cleveland, Ohio, Jun. 22–26, 1981, A.G. Walton, Ed., Elsevier Scientific Publishing Company, Amsterdam, pp. 185–197 (1981).

Bachman, K., et al., "Construction of plasmids carrying the cI gene of bacteriophage λ," *Proc. Nat. Acad. Sci. USA* 73(11):4174–4178 (1976).

Beggs, J.D., "Multiple–copy yeast plasmid vectors, in Molecular Genetics in Yeast," Alford Benzon Symposium No. 16 (Jun. 15–19, 1980), Von Wettstein, et al., Eds. *Munksgaard*, pp. 383–389 (1981).

Bennetzen, J.L., "An analysis of gene structure and expression in the yeast *Saccharomyces cerevisiae*," University of Washington dissertation (Sep. 23, 1980).

Bennetzen, J.L., and B.D. Hall, "The primary structure of the *Saccharomyces cerevisiae* gene for alcohol dehydrogenase I.," *The Journal of Biological Chemistry* 257(6):3018–3025 (1982).

Birnboim, H.C., and J. Doly, "A rapid alkaline extraction procedure for screening recombinant plasmid DNA," *Nucleic Acids Research* 7(6):1513–1523 (1979).

Bogenhagen, D.F., et al., "A control region in the center of the 5S RNA gene directs specific initiation of transcription: II. The 3' border of the region," *Cell* 19:27–35 (Jan. 1980).

Bolivar, F., et al., "Construction and characterization of new cloning vehicles: II. A multipurpose cloning system," *Gene* 2:95–113 (1977).

Clarke, L., and J. Carbon, "A colony bank containing synthetic Col E1 hybrid plasmids representative of the entire *E. coli* genome," *Cell* 9:91–99, (1976).

Corden, J., et al., "Expression of cloned genes in new environment: promoter sequences of eukaryotic protein-coding genes," *Science* 209:1406–1414 (Sep. 1980).

Davis, R.W., "Genetic engineering of yeast for production of specific proteins," American Chemical Society, 179th ACS National Meeting, Houston, Texas, Mar. 24–28, 1980, *Abstract No. 63*, published circa Jan. 27, 1980.

Dickson, R.C., "Expression of a foreign eukaryotic gene in *Saccharomyces cerevisiae*: β–galactosidase from *Kluyveromyces lactis,*" *Gene* 10:347–356 (Sep. 1980).

Dubois, M.–F., et al., "Excretion of hepatitis B surface antigen particles from mouse cells transformed with cloned viral DNA," *Proc. Nat. Acad. Sci. USA* 77:4549–4553 (1980).

*Encyclopaedia Brittanica*, vol. 23, pp. 879–880 (1970), describes "yeast."

Errede, B., et al., "Mating signals control expression of mutations resulting from insertion of a transposable repetitive element adjacent to diverse yeast genes," *Cell* 25:427–436 (Nov. 1980) Part 2.

Faye, G., et al., "Deletion mapping of sequences essential for in vivo transcription of the iso–1–cytochrome c gene," *Proc. Nat. Acad. Sci. USA* 78:2258–2262 (Apr. 1981).

Fried, H.M., and J.R. Warner, "Cloning of yeast gene for trichodermin resistance and ribosomal protein L3," *Proc. Nat. Acad. Sci. USA* 78(1):238–242 (Jan. 1981).

Gill, G.S., et al., "Synthesis of higher eukaryotic proteins in yeast, in Recombinant DNA," Proceedings of the Third Cleveland Symposium on Macromolecules, Cleveland, Ohio, Jun. 22–26, 1981, A.G. Walton, Ed., Elsevier Scientific Publishing Company, Amsterdam, pp. 213–227 (1981).

Gerbaud, C., et al., "High frequency of yeast transformation by plasmids carrying part or entire 2–μm yeast plasmid," *Gene* 5:233–253 (1979).

Glover, D.M., *Genetic Engineering: Cloning DNA*, pp. 1–78, Chapman and Hall, New York (1980).

Goeddel, D.V., et al., "Direct expression in *Escherichia coli* of a DNA sequence coding for human growth hormone," *Nature* 281:544–548 (1979).

Goeddel, D.V., et al., "Synthesis of human fibroblast interferon by *E. coli,*" *Nucleic Acids Research* 8(18):4057–4074 (1980).

Guarente, L., Tenth International Conference of Yeast Genetics and Molecular Biology, Louvain–La–Neuve, Belgium, Sep. 8–12, 1980, *Abstract No. 112*, p. 32.

Guarente, L., and M. Ptashne, "Fusion of *Escherichia coli* lacZ to the cytochrome c gene of *Saccharomyces cerevisiae,*" *Proc. Nat. Acad. Sci. USA* 78(4):2199–2203 (Apr. 1981).

Hamer, D.H., and P. Leder, "SV40 recombinants carrying a functional RNA splice junction and polyadenylation site from the chromosomal mouse $\beta^{maj}$ globin gene," *Cell* 17:737–747 (1979).

Hamer, D.H., et al., "SV40 recombinants carrying rabbit β–globin gene coding sequences," *Cell* 17:725–735 (1979).

Hamer, D.H., "A mouse globin gene promoter is functional in SV40," *Cell* 21:697–708 (Oct. 1980).

Hartley, J.L., and J.E. Donelson, "Nucleotide sequence of the yeast plasmid," *Nature* 286:860–864 (Aug. 28, 1980).

Henikoff, S., and C.E. Furlong, "Sequence of a Drosophila DNA segment that functions in *Saccharomyces cerevisiae* and its regulation by a yeast promoter," *Nucleic Acids Research* 11(3):789–800 (1983).

Hinnen, A., and B. Meyhack, "Vectors for cloning in yeast," *Current Topics in Microbiology and Immunology* 96:101–117 (1982).

Holland, M.J., et al., "The primary structure of two yeast enolase genes," *The Journal of Biological Chemistry* 256(3):1385–1395 (Feb. 10, 1981).

Hollenberg, C.P., "The expression of bacterial antibiotic resistance genes in the yeast *Saccharomyces cerevisiae*," in: *Plasmids of Medical, Environmental and Commercial Importance*, Timmis, K.N., and A. Puhler (Eds.), Elsevier/North–Holland Biomedical Press, pp. 481–492 (1979).

Hollenberg, C.P., "The expression in *Saccharomyces cerevisiae* of bacterial β–lactamase and other antibiotic resistance genes integrated in a 2–μm DNA vector," ICN–UCLA *Simp. Mol. Cell Biol.* 15:325–338 (1979).

Hollenberg, C.P., "Cloning with 2–λm DNA vectors and the expression of foreign genes in *Saccharomyces cerevisiae,*" *Current Topics Microbiol. Immunol.* 96:119–144 (1982).

Jimenez, A., and J. Davies, "Expression of a transposable antibiotic resistance element in Saccharomyces," *Nature* 287:869–871 (Oct. 30, 1980).

Kozak, M., "Mechanism of mRNA recognition by eukaryotic ribosomes during initiation of protein synthesis," *Current Topics in Microbiology and Immunobiology* 93:81–123 (1981).

Martial, J.A., et al., "Human growth hormone: Complementary DNA cloning and expression in bacteria," *Science* 205:602–607 (1979).

Maxam, A.M., and W. Gilbert, "Sequencing end–labeled DNA with base–specific chemical cleavages," *Methods in Enzymology* 65:499–560 (1980).

McNeil, J.B., and J.D. Friesen, "Expression of the *Herpes simplex* virus thymidine kinase gene in *Saccharamoyces cerevisiae,*" *Mol. Gen. Genet.* 184:386–393 (Dec. 1981).

Miller, J.H., "Experiments in Molecular Genetics," Cold Spring Harbor Laboratory, Cold Spring Harbor, N.Y., pp. 431–433 (1972).

Miozzari, G., et al., "Tryptophan biosynthesis and *Saccharomyces cerevisiae*: control of the flux through the pathway," *Journal of Bacteriology* 134(1):48–59 (1978).

Montgomery, D.L., et al., "Identification and isolation of the yeast cytrochrome c gene," *Cell* 14:673–680 (1978).

Montgomery, D.L., et al., "Isolation and sequence of the gene for iso–2–cytochrome c in *Saccharomyces cerevisiae,*" *Proc. Nat. Acad. Sci. USA* 77(1):541–545 (Jan. 1980).

Mulligan, R.C., et al., "Synthesis of rabbit β–globin and cultured monkey kidney cells following infection with SV40 β–globin recombinant genome," *Nature* 277:108–114 (1979).

Mulligan, R.C., and P. Berg, "Expression of a bacterial gene in mammalian cells," *Science* 209:1422–1427 (1980).

Muzyczka, N., "Construction of an SV40–derived cloning vector," *Gene* 11:63–77 (1980).

Nakamura, K., and M. Inouye, "DNA sequence of the *Serratia marcescens* lipoprotein gene," *Proc. Nat. Acad. Sci. USA* 77(3):1369–1373 (Mar. 1980).

Nasmyth, K., "Eukaryotic gene cloning and expression in yeast," *Nature* 274:741–743 (1978).

Ng, R., and J. Abelson, "Isolation and sequence of the gene for actin in *Saccharomyces cerevisiae*," *Proc. Nat. Acad. Sci. USA* 77(7):3912–3916 (Jul. 1980).

Old, R.W., and S.B. Primrose, "Principals of Gene Manipulation: An introduction to genetic engineering," Second Edition, University of California Press, pp. 4, 62–68, and 163 (1981).

Roman, H., "Development of yeast as an experimental organism," in *The Molecular Biology of the Yeast Saccharomyces*, J.M. Strathern, et al., Eds., Cold Spring Harbor Laboratory, New York, pp. 1 and 5 (1981).

Rose, M., et al., "Yeast genes fused to β–galactosidase in *Escherichia coli* can be expressed normally in yeast," *Proc. Nat. Acad. Sci. USA* 78(4):2460–2464 (Apr. 1981).

Seeburg, P.H., et al., "Synthesis of growth hormone by bacteria," *Nature* 276:795–798 (1978).

Shalit, P., et al., "Physical analysis of the CYC1–sup4 interval in *Saccharomyces cerevisiae*," *Molecular and Cellular Biology* 1(3):228–236 (Mar. 1981).

Sherman, F., et al., "Mutants of yeast initiating translation of iso–1–cytochrome c within a region spanning 37 nucleotides," *Cell* 20:215–222 (May 1980).

Shine, J., et al., "Expression of cloned β–endorphin gene sequences by *Escherichia coli*," *Nature* 285:456–461 (Jun. 1980).

Smith, M., et al., "Sequence of the gene for iso–1–cytochrome c in *Saccharomyces cerevisiae*," *Cell* 16:753–761 (1979).

St. John, T.P., "The organization and transcription of the *Saccharomyces cerevisiae* galactose gene cluster," *Dissertation Abstracts International* 41(05):1618–B (Nov. 15, 1980).

St. John, T.P., "The organization and transcription of the *Saccharomyces cerevisiae* galactose gene cluster," Stanford University dissertation, dated May 1980; published Nov. 15, 1980, by University Microfilms International.

Stewart, II, W.E., *The Interferon System*, Springer–Verlag, New York, pp. 17–19 (1979).

Struhl, K. and R.W. Davis, "DNA sequence analysis of his3 promoter mutants," in *The Molecular Biology of Yeast*, J. Broach, et al., Eds., Cold Spring Harbor Laboratory, New York, p. 144 (1979).

Struhl, K. "Deletion mapping a eukaryotic promoter," *Proc. Nat. Acad. Sci. USA* 78(7):4461–4465 (Jul. 1981).

Sures, I., et al., "Nucleotide sequence of human preproinsulin complementary DNA," *Science* 208:57–59 (1980).

Valenzuela, P., et al., "Synthesis and assembly of hepatitis B virus surface antigen particles in yeast," *Nature* 295:347–350 (1982).

van den Berg, J., et al., "Transcription of a rabbit β–globin gene in yeast cells," in *The Molecular Biology of Yeast*, J. Broach, et al., Eds., Cold Spring Harbor Laboratory, New York, p. 162 (1979).

van Ooyen, A., et al., "Comparison of total sequence of a cloned rabbit β–globin gene and its flanking regions with a homologous mouse sequence," *Science* 206:337–344 (1979).

Veit, B., University of Washington term paper (Dec. 1980).

Villa–Komaroff, L., et al., "A bacterial clone synthesizing proinsulin," *Proc. Nat. Acad. Sci. USA* 75(8):3727–3731 (1978).

Wallace, R.B., et al., "Directed deletion of a yeast transfer RNA intervening sequence," *Science* 209:1396–1400 (Sep. 19, 1980).

Wasylyk, B., et al., "Specific in vitro initiation of transcription on conalbumin and ovalbumin genes and comparison with adenovirus–2 early and late genes," *Nature* 285:367–373 (Jun. 1980).

Weck, P.K., et al., "Antiviral activities of hybrids of two major human leukocyte interferons," *Nucleic Acids Research* 9(22):6153–6166 (1981).

Wetzel, R., et al., "Production of biologically active $N^\alpha$–desacetylthymosin $\alpha_1$ in *Escherichia coli* through expression of a chemically synthesized gene," *Biochemistry* 19(26):6096–6104 (1980).

EXPRESSION OF POLYPEPTIDES IN YEAST

This application is a continuation application based on prior application Ser. No. 08/383,668, filed Feb. 3, 1995 (abandoned), which is a continuation of Ser. No. 08/198, 535, filed on Feb. 18, 1994 (abandoned), which is a continuation of Ser. No. 08/089,419, filed Jul. 9, 1993, (abandoned), which is a continuation of Ser. No. 07/708, 828, filed May 29, 1991 (abandoned), which is a continuation of Ser. No. 07/349,918, filed May 9, 1989 (abandoned), which is a continuation of Ser. No. 07/284,774, filed Dec. 12, 1988 (abandoned), which is a continuation of Ser. No. 07/173,008, filed Mar. 28, 1988 (abandoned), which is a continuation of Ser. No. 06/764,145, filed Aug. 9, 1985 (abandoned), which is a continuation of Ser. No. 06/237, 913, filed Feb. 25, 1981 (abandoned).

FIELD OF THE INVENTION

This invention relates to the production, via recombinant DNA technology, of useful polypeptides in *Saccharomyces cerevisiae* (yeast), and to the means and methods of such production.

BACKGROUND OF THE INVENTION

The publications and other materials referred to herein to illuminate the background of the invention and, in particular cases, to provide additional detail respecting its practice are incorporated herein by reference, and, for convenience, are numerically referenced and grouped in the appended bibliography.

Recombinant DNA Technology

With the advent of recombinant DNA technology, the controlled microbial production of an enormous variety of useful polypeptides has become possible. Already in hand are bacteria modified by this technology to permit the production of such polypeptide products as somatostatin (1), the component A and B chains of human insulin (1), human proinsulin (2), thymosin alpha 1 (3), human growth hormone (4), human (5) and hybrid (6) leukocyte and fibroblast (7) interferons, as well as a number of other products. The continued application of techniques already in hand is expected in the future to permit bacterial production of a host of other useful polypeptide products, including other hormones, enzymes, immunogens useful in the preparation of vaccines, immune modulators and antibodies for diagnostic and drug-targeting applications.

The workhorse of recombinant DNA technology is the plasmid, a non-chromosomal loop of double-stranded DNA found in bacteria and other microbes, oftentimes in multiple copies per cell. Included in the information encoded in the plasmid DNA is that required to reproduce the plasmid in daughter cells (i.e., an "origin of replication") and, ordinarily one or more selection characteristics such as, in the case of bacteria, resistance to antibiotics, which permit clones of the host cell containing the plasmid of interest to be recognized and preferentially grown under selective conditions. The utility of plasmids lies in the fact that they can be specifically cleaved by one or another restriction endonuclease or "restriction enzyme", each of which recognizes a different site on the plasmid DNA. Thereafter heterologous genes or gene fragments may be inserted into the plasmid by endwise joining at the cleavage site or at reconstructed ends adjacent to the cleavage site. DNA recombination is performed outside the cell, but the resulting "recombinant" plasmid can be introduced into it by a process known as transformation and large quantities of the heterologus gene-containing recombinant plasmid are then obtained by growing the transformant. Moreover, where the gene is properly inserted with reference to portions of the plasmid which govern the transcription and translation of the encoded DNA information, the resulting expression vehicle can be used to actually produce the polypeptide sequence for which the inserted gene codes, a process referred to as expression.

Expression is initiated in a region known as the promoter which is recognized by and bound by RNA polymerase. The polymerase travels along the DNA, transcribing the information contained in the coding strand from its 5' to 3' end into messenger RNA which is in turn translated into a polypeptide having the amino acid sequence for which the DNA codes. Each amino acid is encoded by a nucleotide triplet or "codon" within what may for present purposes be referred to as the "structural gene", i.e., that part which encodes the amino acid sequence of the expressed product. After binding to the promoter, the RNA polymerase, transcribes a 5' leader region of messenger RNA, then a translation initiation or "start signal" (ordinarily ATG, which in the resulting messenger RNA becomes AUG), then the nucleotide codons within the structural gene itself. So-called stop codons are transcribed at the end of the structural gene whereafter the polymerase may form an additional sequence of messenger RNA which, because of the presence of the stop signal, will remain untranslated by the ribosomes. Ribosomes bind to the binding site provided on the messenger RNA, and themselves produce the encoded polypeptide, beginning at the translation start signal and ending at the previously mentioned stop signal. The resulting product may be obtained by lysing the host cell and recovering the product by appropriate purification from other microbial protein or, in particular instances, possibly by purification from the fermentation medium into which the product has been secreted.

Plasmids employed in genetic manipulations involved in the construction of a vehicle suitable for the expression of a useful polypeptide product are referred to as DNA transfer vectors, Thus, employing restriction enzymes and associated technology, gene fragments are ordered within the plasmid in in vitro manipulations, then amplified in vivo in the transformant microbes into which the resulting, recombinant plasmid has been 'transferred'. A "DNA expression vector" comprises not only a structural gene intended for expression but also a promoter and associated controls for effecting expression from the structural gene. Both transfer and expression vectors include origins of replication. Transfer vectors must and expression vectors may also include one or more genes for phenotypic selection of transformant colonies.

Thus far, the useful products of expression from recombinant genes have fallen into two categories. In the first, a polypeptide having the amino acid sequence of a desired end product is expressed directly, as in the case of human growth hormone and the interferons referred to above. In the second, the product of expression is a fusion protein which includes not only the amino acid sequence of the desired end product but also one or more additional lengths of superfluous protein so arranged as to permit subsequent and specific cleavage away of the superfluous protein and so as to yield the desired end product. Thus, cyanogen bromide cleavage at methionine residues has yielded somatostatin, thymosin alpha 1 and the component A and B chains of human insulin from fusion proteins; enzymatic cleavage at defined residues has yielded beta endorphin (8).

A "biocompetent polypeptide", as that term is used herein, refers to a product exhibiting bioactivity akin to that of a polypeptide innately produced within a living organism for a physiological purpose, as well as to intermediates which can be processed into such polypeptides, as by cleavage away of superfluous protein, folding, combination (as in the case of the A and B chains of human insulin), etc.

Saccharomyces cerevisiae

The cells of Saccharomyces cerevisiae, or yeast, are, like those of mammalian organisms, eukaryotic in nature as distinguished from the prokaryotic nature of bacteria. With regard to mechanisms for the expression of genetic information, eukaryotes are distinguished from bacteria by:

(1) chromosomes which are organized in 140 base pair units, each containing two molecules each of histones H2A, H2B, H3, and H4.

(2) Transcription of the protein-encoding gene by the alpha-amanitin sensitive RNA polymerase II.

(3) Post transcriptional addition of Gppp and polyadenylic acid to the 5' and 3' termini of mRNA molecules.

(4) Transport of newly completed mRNA from the nuclei where they are transcribed to the cytoplasm where they are translated.

(5) Some but not all eukaryotic genes contain intervening sequences (introns) which make them non-colinear with the corresponding mature mRNA molecule. The initial transcription products of these genes contain the intron sequence which is spliced out subsequently in the formation of a finished mRNA molecule.

The nucleotide sequences of all eukaryotic cells are transcribed, processed, and then translated in the context described above. There are reasons to believe that expression of eukaryotic genes may proceed with greater efficiency in yeast than in E. coli because yeast is a eukaryote cell.

A number of workers have previously expressed, or attempted to express, foreign genes in yeast transformants. Thus, attempted expression from a fragment comprising both a promoter and structural gene for rabbit globin is reported (9) to have yielded partial mRNA transcripts, seemingly unaccompanied either by translation into protein or maturation (intron elimination) of the message. A gene coding for Drosophila GAR tranformylas (yeast ADE8), an enzyme in the adenine synthesis pathway, is reported to have been expressed under the control of its own promoter (10). A number of yeast proteins have hitherto been expressed in yeast via recombinant plasmids (see, eg., 12). In the experiments, as in the Ade-8 case earlier discussed, expression occurred under the selective pressure of genetic complementation. Thus, each expression product was required for growth of the host strains employed, mutants whose chromosomal DNA was defective in the structural gene(s) from which expression occurred.

The availability of means for the production in yeast of proteins of choice could provide significant advantages relative to the use of bacteria for the production of polypeptides encoded by recombinant DNA. Yeast has been employed in large scale fermentations for centuries, as compared to the relatively recent advent of large scale E. coli fermentation. Presently, yeast can be grown to higher densities than bacteria, and is readily adaptable to continuous fermentation processing. Many critical functions of the organism, e.g., oxidative phosphorylation, are located within organelles, and hence not exposed to the possible deleterious effects of the organism's overproduction of foreign proteins. As a eukaryotic organism, yeast may prove capable of glycosylating expression products where important to enhanced bioactivity. Again, it is possible that as eukaryotic organisms, yeast cells will exhibit the same codon preferences as higher organisms, tending toward more efficient production of expression products from mammalian genes or from complementary DNA (cDNA) obtained by reverse transcription from, e.g., mammalian messenger RNA. Until the present invention, however, attempts to produce biocompetent expression products other than those required for cellular growth have proven largely unsuccessful.

BRIEF SUMMARY OF THE INVENTION

The present invention provides DNA expression vectors capable, in transformant strains of yeast, of expressing biologically competent (preferably pharmacologically active) polypeptides under the control of genetically distinct yeast promoters, the polypeptides being ordinarily exogenous to yeast and other than those required for growth of the transformant. The invention also provides DNA transfer vectors for the transformation of yeast strains with genes encoding biocompetent polypeptides, as well as novel yeast organisms and cultures thereof incorporating such vectors and methods for the formation of the same. The structural genes incorporated in the expression vectors and transformant organisms of the invention are under the control of genetically distinct yeast promoters, i.e., promoters different from those evolutionarily associated with the subject structural genes.

The manner in which these and other objects and advantages of the invention are obtained will become apparent from the detailed description which follows, and from the accompanying drawings in which.

In the Figures and throughout, the letters A, T, C and G respectively connote the nucleotides containing the bases adenine, thymine, cytosine and guanine. Only the coding strands of plasmids and gene fragments are depicted. Though obviously not to scale, the representations of plasmids depict the relative position of restriction enzyme cleavage sites ("Eco RI", "HindIII" etc.) and other functions such as tetracycline resistance ("Tc"") and ampicillin resistance ("Ap'").

DESCRIPTION OF PREFERRED EMBODIMENTS

Preferred embodiments of the invention are obtained by bringing an exogenous gene under the control of a yeast promoter carried by a plasmid suitable for the transformation of yeast. Essentially any yeast strain suited for the selection of transformants may be employed. In order to achieve direct expression of the desired end product or an intermediate therefor, rather than a fusion comprising portions of the yeast protein whose expression is controlled by the promoter in wild-type strains, the parental plasmid is resected toward the promoter in the direction opposite that of transcription, so as to excise the ATG triplet which initiates translation of mRNA encoding the yeast protein referred to.

An ordinarily exogenous gene, with its associated start signal, may then be inserted at the endpoint of the resection, and thus positioned for direct expression under the control of the yeast promoter. This and other aspects of the invention are illustrated in the description of preferred embodiments which follow.

METHODS

Materials

All DNA restriction and metabolism enzymes were purchased from New England Biolabs except for exonuclease Bal 31 and bacterial alkaline phosphatase, which were obtained from Bethesda Research Laboratories. DNA restriction enzyme and metabolic enzymes were used in conditions and buffers described by their respective manufacturers. ATP and the deoxynucleoside triphosphates dATP, dGTP, dCTP and dTTP were purchased from PL Biochemicals. Eco RI, Bam HI, Hind III and Xho I linkers were obtained from Collaborative Research, Inc. [$\alpha$-$^{32}$P] was obtained from New England Nuclear Corp.

DNA Preparation and Transformation

Purification of covalently closed circular plasmid DNAs from $E.$ $coli$ (13) and yeast (14) plus the transformation of $E.$ $coli$ (15) was as previously described. Transformation of yeast was as described by Hsiao and Carbon (16) with the exception that 1.2 M Sorbitol was used instead of 1.0 M Sorbitol. $E.$ $coli$ miniscreens were as described by (17).

Strains and Media $E.$ $coli$ strain JA300 (thr leuB6 thi thyA trpC1117 hsdM$^-$ hsdR$^-$ str$^R$) (18) was used to select for plasmids containing functional trpI gene. $E.$ $coli$ K-12 strain 294 (ATCC no. 31446) (19) was used for all other bacterial transformation. Yeast strains RH218 having the genotype (a trpI gal2 suc2 ma1 CUPI) (20) and GM-3C-2 ($\alpha$, leu 2-3, leu 2-112, trp 1-1, his 4-519, cyc 1-1, cyp 3-1) (21) were used for yeast transformations. Yeast strain RH 218 has been deposited without restriction in the American Type Culture Collection, ATCC No. 44076.

M9 (minimal medium) with 0.25 percent casamino acids (CAA) and LB (rich medium) were as described by Miller (22) with the addition of 20 $\mu$g/ml ampicillin (Sigma) after media is autoclaved and cooled. Yeast were grown on the following media: YEPD contained 1 percent yeasts extract, 2 percent peptone and 2 percent glucose ±3 percent Difco agar. YNB+CAA contained 6.7 grams of yeast nitrogen base (without amino acids) (YNB),(Difco), 10 mg of adenine, 10 mg of uracil, 5 grams CAA, 20 grams glucose and ±30 grams agar per liter. The selection of ADH promoter active fragments occurred on YEPGE plates containing 3 percent glycerol and 2 percent ethanol substituted for glucose in the YEPD formula. Leucine prototrophy was determined on plates containing 6.7 gms YNB, 20 gms glucose, 50 mgs histidine and 50 mgs trytophan and 30 gms Difco agar per L.

Construction and Identification of ADH Promoter Deletions pY9T6 was digested with Sau3A then run on a preparative 1 percent agarose gel. The 1600 bp fragment containing the ADH promoter region was cut from the gel, electroeluted then purified on a diethylamino cellulose (DE52, Whatman) column before ethanol precipitation. Fragment DNA was resuspended in DNA Polymerase I (Klenow fragment) buffer supplemented with the four deoxyribonucleoside triphosphates in a final concentration of 80 $\mu$M. Polymerase I was added and the thirty-minute room temperature reaction was terminated by ethanol precipitation of the DNA. An equal molar amount of BamHI and HindIII linker was added to the resuspended Sau3A fragment so that each linker was in a 20:1 molar excess to the large DNA fragment. $T_4$ DNA ligase was added and the 12 hour reaction occured at 12 degrees centigrade. After ethanol precipitation and resuspension in the appropriate buffer, the DNA was digested with BamHI, then HindIII. The now larger promoter-containing fragment was purified away from the unattached linkers by passage through a 10 ml sizing column before ethanol precipitation. This DNA fragment was then ligated in pBR322 previously isolated as missing the HindIII-to-BamHI restriction fragment. $E.$ $coli$ strain RR1 was transformed to ampicillin resistance using part of this ligation mix. After quick screen analysis of a number of recombinant plasmids, pJD221 which had the insert with the HindIII linker added to the end of the fragment closest to the ATG of the ADH structural gene was isolated by plasmid preparation.

pJD221 was linearized with HindIII and the resulting fragment than successively treated with exonuclease III and $S_1$ nuclease. The ends of these deleted plasmids were then made blunt using the Klenow fragment of DNA Polymerase I (see procedure above). After ethanol precipitation the ends of the DNA were ligated with XhoI linkers in a 12 hour reaction mixture. After digestion of resulting ligation mix with XhoI, plasmid solution was run in a 0.5 percent preparative agarose gel. DNA bands were cut from the gel, electroluted, then passed through a DE52 column before ethanol precipitation. Linear plasmid was circularized using T4 DNA Ligase. The resulting ligation mix was used to transform $E.$ $coli$ strain RR1 to ampicillin resistance. All such colonies were pooled together. The resulting single plasmid pool was cut with XhoI and BamHI, then run on a preparative 0.7 percent agarose gel. The 1500 bp bands containing the ADH promoter region were cut from the gel, electroeluted then passed through a DE52 column before ethanol precipitation and ligation into the vector pYecycIΔx+1. This plasmid had previously been isolated from an agarose gel as having lost the XhoI to BamHI restriction fragment described in the Figure. The resulting ligation was used to transform $E.$ $coli$ strain RRI to ampicillin resistance. Colonies were mixed for preparation of a plasmid pool which was then used to transform yeast strain GM-3C-2 to leucine prototrophy. Plasmids were then isolated from leucine prototrophs able to grow on glycerol plates. One plasmid, pACF 301, was found to contain a deletion extending toward the ATG of the ADH1 structural gene, leaving intact the first five triplets of the structural gene and the AC of the ACC of $Thr_6$ (FIG. 2$b$). This plasmid was digested with XhoI then treated with exonuclease Bal31 for 15 and 30 seconds (two different aliquots). Resulting plasmids were pooled, ethanol precipitated and then treated with DNA Polymerase I (reaction described above) so that all DNA ends were made blunt. EcoRI linkers were then added to the DNA solution and ligation allowed to proceed for 12 hours. After digestion with EcoRI and BamHI, ligation mix was run on a preparative agarose gel. A DNA band about 1500 bp in size was cut from the gel, electroeluted then passed through a sizing column before ethanol precipitation. This DNA was then ligated into the linear pBR322 DNA previously isolated as missing the EcoRI-to-BamHI restriction fragment. This ligation mix was used to transform $E.$ $coli$ strain 294 to ampicillin resistance. Plasmids isolated from these colonies are referred to as the pGBn plasmid series.

Miniscreen analysis of a number of different recombinant plasmids from the pGBn plasmid series indicated that nine particular plasmids had small Bal 31 generated deletions toward the ADH promoter region through the ATG of the ADH structural gene. All nine plasmids were digested with EcoRI, then end labeled by incubation with ($\alpha^{32}$P)dATP and DNA polymerase I (conditions as described above). After ethanol precipitation, seven plasmids were digested with AluI then electrophoresed on a 20 percent acrylamide-urea sequencing gel. $^{32}$P-labelled plasmid DNAs from pGB904 and pGB906 were cut with BamHI then run on a preparative gel. Labelled fragments containing the ADH promoter region were excised from the gel, electroluted, passed through a DE52 column before ethanol precipitation. These two resuspended fragments (from plasmids pGB904 and pGB906) were then subjected to the G+A and T+C sequence specific degradation reactions described by Maxam and Gilbert (procedure 11 and 12 respectively (23)). These sequencing reaction products were electrophoresed along with labeled fragments from pGB905, pGB914, pGB917, pGB919 and pGB921 on the thin 20 percent acrylamide sequencing gel (described in the sequencing reference). Autoradiography was as described. This procedure allowed the determination of the extent of deletion of ADH promoter region as this region had previously been sequenced using all four Maxam-Gilbert sequencing reactions (J. Bennetzen, Ph.D Thesis, University of Washington, 1980).

Expression Vector Construction

10 μg of YRp7 (24–26) was digested with EcoRI. Resulting sticky DNA ends were made blunt using DNA Polymerase I (Klenow fragment). Vector and insert were run on 1 percent agarose (SeaKem) gel, cut from the gel, electroeluted and 2× extracted with equal volumes of chloroform and phenol before ethanol precipitation. The resulting blunt end DNA molecules were then ligated together in a final volume of 50 μl for 12 hours at 12° C. This ligation mix was then used to transform E. coli strain JA300 to ampicillin resistance and tryptophan prototrophy. Plasmids containing the TRPI gene in both orientations were isolated. pFRW1 had the TRPI gene in the same orientation as YRp7 while pFRW2 had the TRPI gene in the opposite orientation.

10 μg of pFRW1 and 10 μg of YRp7 were digested with HindIII then run in separate lanes on a 1 percent agarose gel. The large HindIII fragment from the pFRW1 lane and the small fragment from the YRp7 lane were eluted from the gel, extracted with phenol and chloroform, ethanol precipitated, then ligated for 12 hours at 15° C. in a final volume of 50 μl. This ligate mix was used to transform JA300 to tryptophan prototrophy and ampicillin resistance. Plasmid (pFRL4) containing a single EcoRI site was then purified.

The pGBm plasmid series was digested with BamHI and EcoRI then run on a 1 percent agarose gel. The ≅1500 bp promoter containing fragment from each lane was cut from the gel, electroeluted, then purified on a 10 ml diethylamino cellulose (Whatman) column before ethanol precipitation.

20 μg of pFRL4 was digested with BamHI and EcoRI then run on a 1 percent agarose gel. The large (≅5 kb) fragment was cut from the gel, electroeluted, 2× extracted with phenol and chloroform before ethanol precipitation. 3 μg of this fragment was then separately ligated with each of the promoter containing fragments for 12 hours at 15° C. in 50 μl ligation mix. E. coli K-12 strain 294 was transformed with the ligation mix to ampicillin resistance and plasmids from each of these different transformation mixtures were purified (pFRPn plasmid genes).

10 μg of pLeIF D (5) was digested with EcoRI then run on a 6 percent acrylamide gel. The 560 bp leukocyte interferon D gene was cut from the gel, electroeluted and 2× extracted with phenol/chloroform before ethanol precipitation. This interferon gene was then ligated into the unique EcoRI site in the pFRPn plasmids previously cut with EcoRI and treated with bacterial alkaline phosphatase. These vectors were then used for BglII restriction analysis and yeast transformations.

Interferon Assay

Extracts of yeast were assayed for interferon by comparison with interferon standards by the cytopathic effect (CPE) inhibition assay (27). Yeast extracts were prepared as follows: Five ml cultures were grown in YNB+CAA until reaching $A_{660}$≅1–2. Cells were collected by centrifugation then resuspended in 600 μl of 1.2 M sorbitol, 10 mM $KH_2PO_4$, pH=6.8 and 1 percent zymolyase 60,000 then incubated at 30° C. for 30 min. Spheroplasts were pelleted at 3000×g for 10 min., then resuspended in 150 μl of 7 M guanidine hydrochloride plus 1 mM phenylmethylsulfonylfouride (PMSF). Extracts were diluted 1,000 fold in PBS buffer (20 mM $NaH_2PO_4$, pH=7.4, 150 mM NaCl, 0.5 percent BSA) immediately before the assay.

RESULTS

Construction of a Vector for Insertion of a Series of Promoter Fragments and for Insertion of a Gene to be Expressed To design a plasmid vector for autonomous replication in yeast, it is necessary to have both an origin of replication and a gene present for selection in yeast. Furthermore, the plasmid must contain a bacterial plasmid origin of replication and a means of selection in bacteria (e.g., an antibiotic resistance gene). With these requirements a plasmid can be constructed and modified in vitro using recombinant DNA techniques, amplified in bacteria, preferably E. coli, and finally transformed into yeast.

Figure 1:
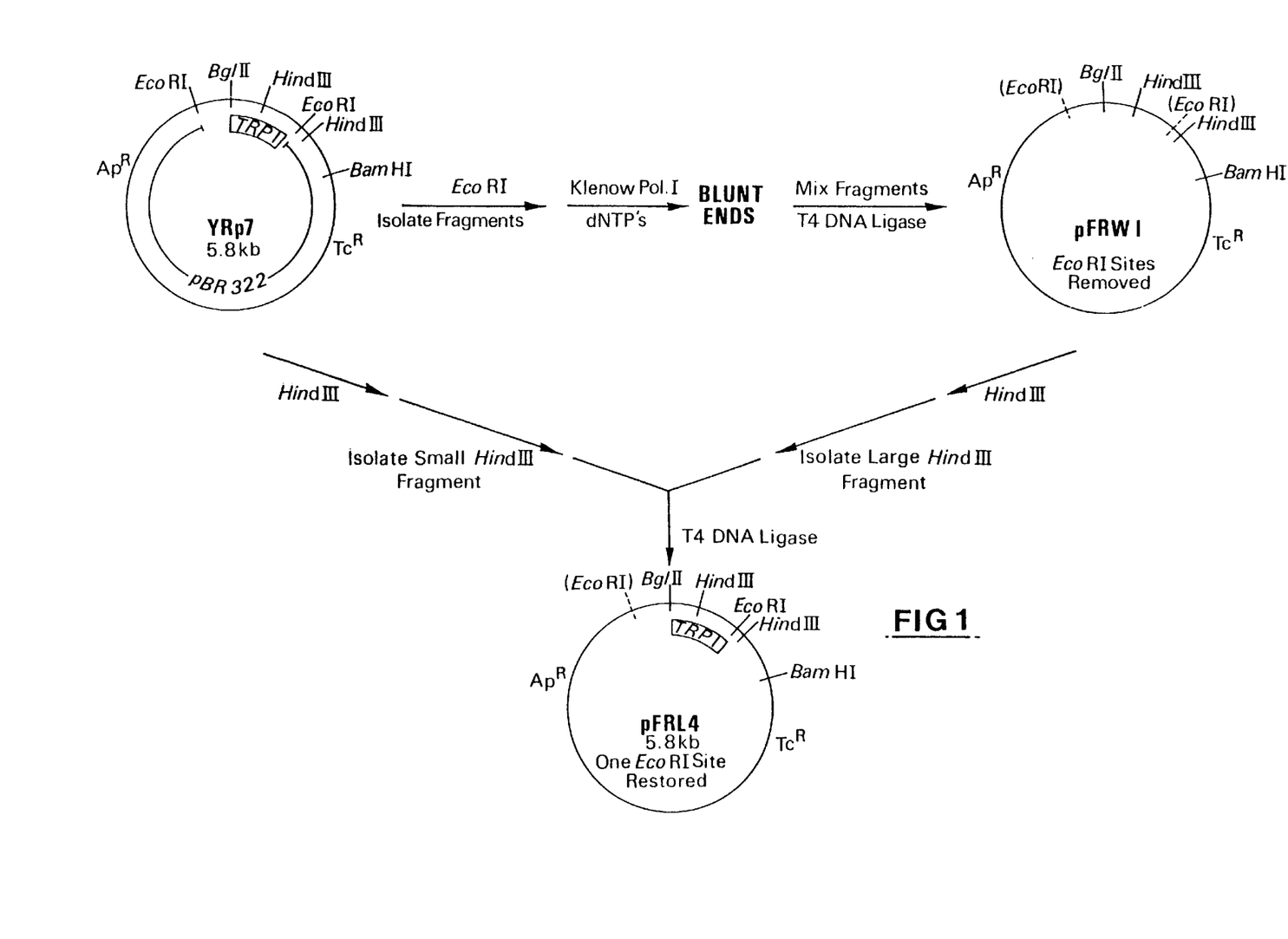
FIG. 1 schematically illustrates the construction of a DNA transfer vector having a single Eco RI restriction site for the subsequent insertion of a yeast promoter and comprising both bacterial and yeast origins of replication and selection phenotypes.

Such a vector is shown in FIG. 1 and is designated YRp7 (24–26). It contains a chromosomal origin of replication from yeast (ars1) as well as the TRP1 gene which codes for N-(5'-phosphoribosyl)-anthranilate isomerase (28). The TRP1 yeast gene can complement (allow for growth in the absence of tryptophan) trp1 mutations in yeast (e.g., RH218, see Methods) and can also complement the trpC1117 mutation of E. coli (e.g. JA300) (18). The plasmid is pBR322 (29) based so it also permits growth and selection in E. coli using antibiotic resistance selection.

Since it was necessary to clone into this vector BamHI/EcoRI restriction fragments containing a yeast promoter, it proved convenient to first remove one EcoRI site from the vector. This was done as shown in FIG. 1. The vector YRp7 was cut with EcoRI followed by filling in of the sticky EcoRI ends of both fragments with Klenow DNA polymerase I. The fragments were then blunt end ligated and the resulting DNA was used to transform E. coli JA300 to Trp$^+$ and ampicillin resistance (Ap$^R$). In such a way plasmid pFRW1 was isolated with both EcoRI sites removed.

One EcoRI site was then restored to the plasmid in order that an EcoRI/BamHI fragment could be later cloned into the vector. This was done by cutting both YRp7 and pFRW1 with HindIII followed by the isolation of the fragments indicated. When the small HindIII fragment of YRp7 was put together with the large HindIII fragment of pFRW1, pFRL4 was obtained. It was selected for in E. coli JA300 using Trp$^+$ and Ap$^R$ phenotypes.

Construction of Yeast Alcohol Dehydrogenase (ADH) Promoter Fragments

Figure 2A:
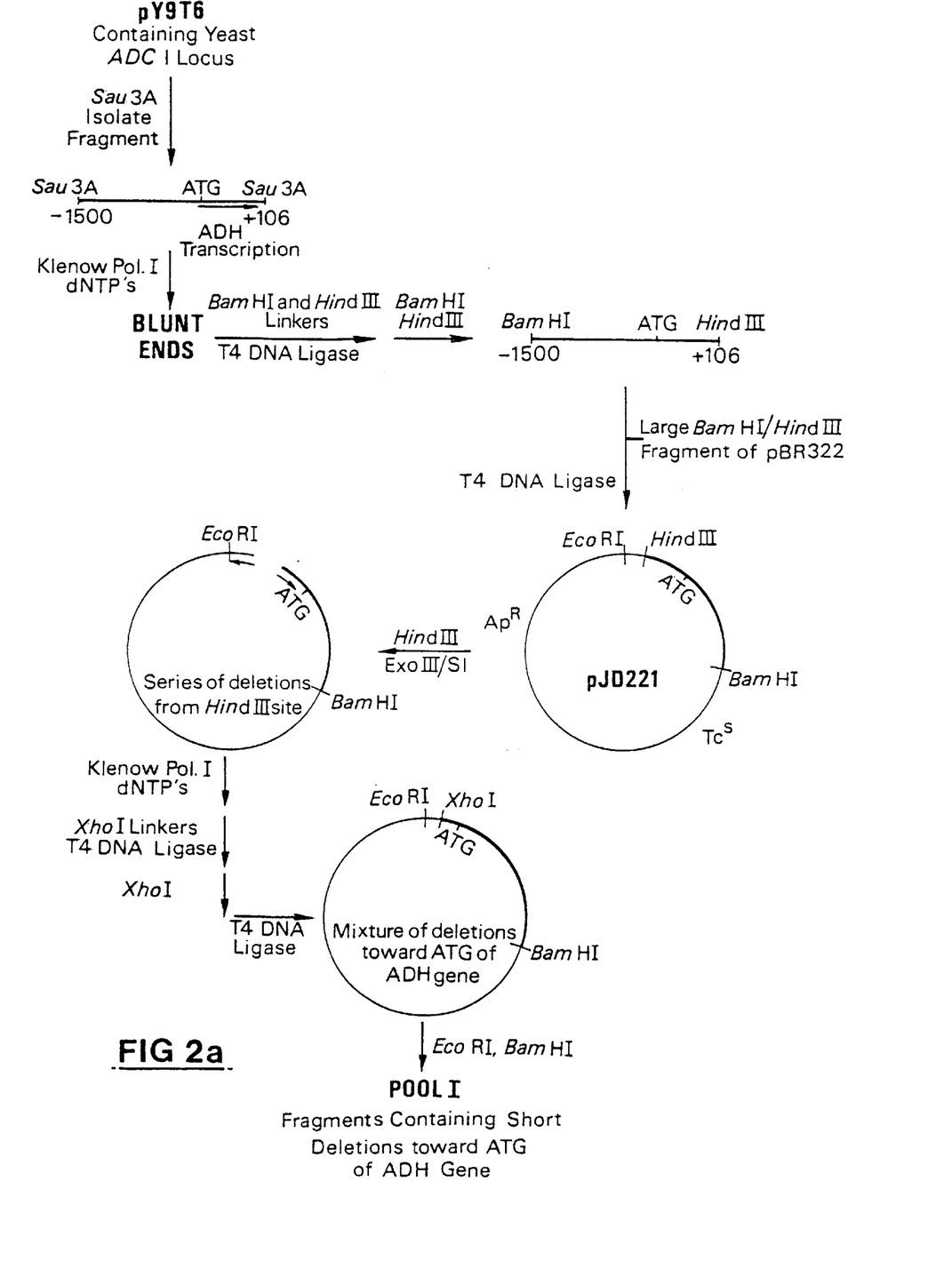
FIG. 2 schematically illustrates the construction of alcohol dehydrogenase promoter fragments for insertion into the transfer vector of FIG. 1.
Figure 2B:
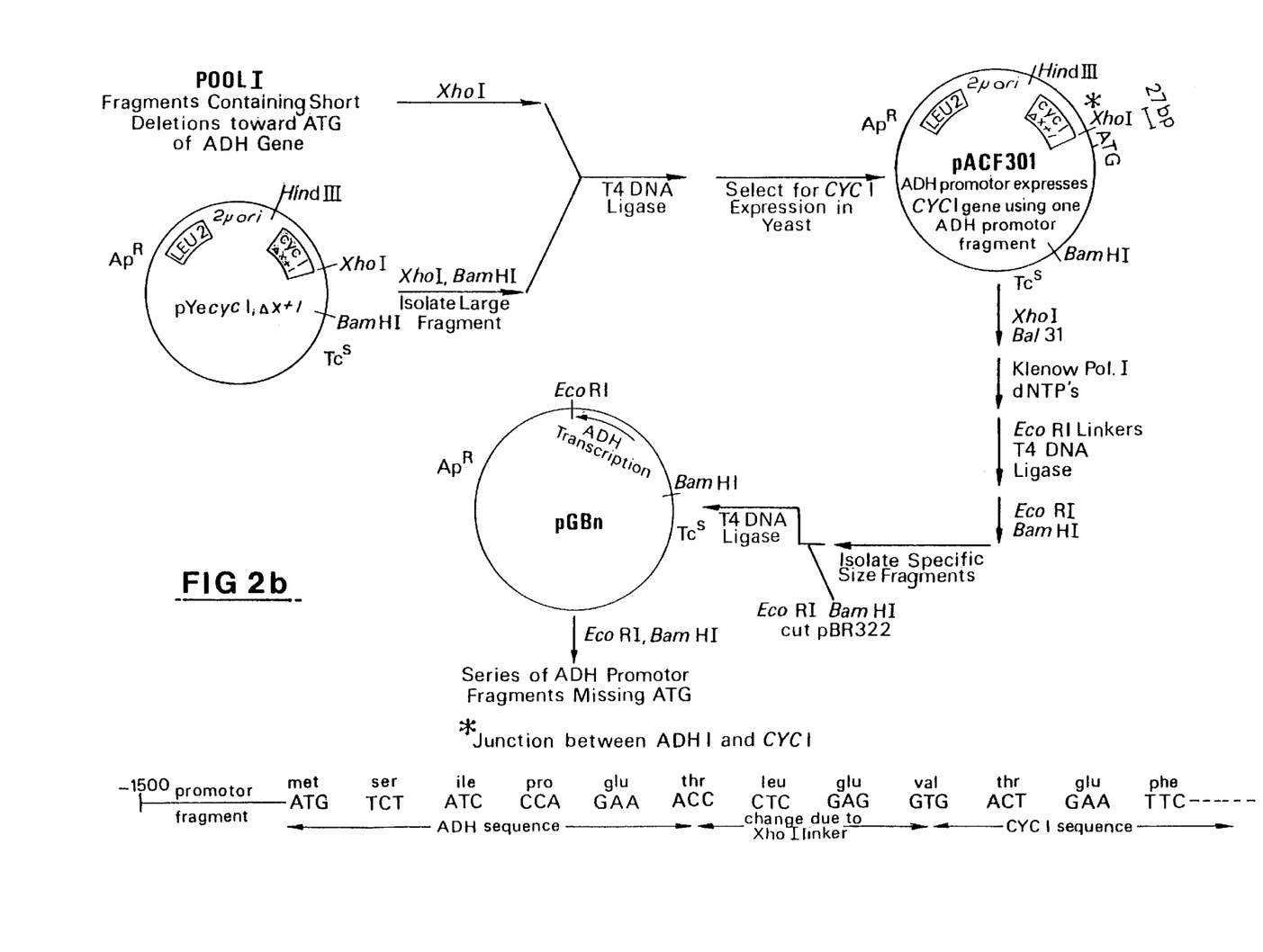

Since it is not known whether certain specific sequences in the leader region preceding structural genes are required for RNA polymerase II binding or what DNA is necessary for ribosome recognition (ribosome binding sites) of the mRNA, promoter fragments from the ADH gene (ADCI) were obtained as described in FIG. 2.

The first step was to show that the 5'-leader DNA sequence of the ADH gene could be used to express another structural gene from yeast without its leader sequence (CYC1). Thus a plasmid which can complement a cyc1 mutation in yeast can be used to isolate the ADH promoter fragment that will result in cyc1 expression. This promoter fragment could then be used to express other eukaryotic genes (eg., the Leukocyte Interferon D gene).

As shown in FIG. 2, pY9T6 containing the ADC1 locus (Bennetzen, supra) was cut with Sau3A to isolate the 5'-flanking sequence of the ADH gene on an approximately 1600 bp fragment. The ATG translation start for the ADH coding sequence is shown with the A at position +1, and transcription goes from left to right as shown. This fragment was blunt ended using Klenow DNA polymerase I followed by a ligation with a mixture of BamHI and HindIII linkers. After cutting with BamHI and HindIII, the fragments were ligated with the large BamHI/HindIII fragment of pBR322. The ligation products were used to transform $E.$ $coli$ to $Ap^R$ and the desired pJD221 was isolated from a transformant colony using a standard miniscreen procedure (see Methods). pJD221 was cut with HindIII and then with exonuclease III and $S_1$ nuclease to remove base pairs toward but not through the ATG of the ADH structural gene.

This procedure also removes base pairs in the opposite direction (toward the EcoRI site) at approximately the same rate. The reaction was designed so as to not remove the ATG of ADH since the ATG of CYC1 was not present in the fragment to be expressed under ADH promoter control. Therefore a complementation of cyc1 yeast would require a functional ADH1-CYC1 fusion protein.

The end-deleted products were treated with Klenow DNA polymerase I to ensure blunt ends followed by the addition of XhoI linkers by blunt end ligation. After XhoI cutting a circular plasmid was regenerated by ligation. Plasmids containing gel-determined, properly sized EcoRI-to-BamHI restriction fragments were digested with XhoI, then ligated with the large XhoI-to-BamHI restriction fragment of plasmid pYecyc 1 Δx+1. After amplification in $E.$ $coli$ RR1 resulting plasmids were used to transform a cyc1 cyc3 leu1 yeast strain to leucine prototrophy on minimal glucose plates. Growing colonies were patched onto glycerol/ethanol plates. Yeast able to grow on such plates require the presence of functional cytochrome-c protein. This can only occur on this plasmid if fragments containing ADH promoter deletions can initiate (in the correct reading frame) translation of the cytochrome c-coding region. Plasmid pACF301 was isolated from one such transformant. The junction between ADH1 and CYC1 is shown at the bottom of FIG. 2b. Six amino acid codons from the ADH sequence were present with 3 new amino acid codons due to the XhoI linker, and the rest represented the CYC1 structural gene. Thus the ADH promoter fragment is expressing a fusion gene product that produces a phenotypically active CYC1 gene fusion product.

In the construction of a yeast expression plasmid, it is desirable that the ATG codon of the non-yeast gene to be expressed be the one belonging to the same non-yeast gene rather than a vector ATG which would lead to the synthesis of an undesired fusion protein. Therefore, it proved appropriate to remove nucleotides through the ATG of the ADH promoter fragment by another series of deletions and supply a new translation start signal with the gene to be expressed. Since the functionality of upstream DNA sequence (−1 to −1500) during the expression process is not known, it was desirable to remove as little sequence as possible upstream from the ATG and to try different fragments lacking both the initially present ATG and various amounts of additional DNA sequence.

These additional promoter fragments were isolated as shown in FIG. 2b. pACF301 was cut with Xhoh and Bal31. After blunt-ending, addition of EcoRI linker, BamHI/EcoRI cutting, and sizing fragments; the correct size class of fragments were ligated with EcoRI/BamHI-cut pBR322. Specific recloned ADH promoter fragments were isolated from plasmids from various $E.$ $coli$ $Ap^R$ transformants.

Figure 3:
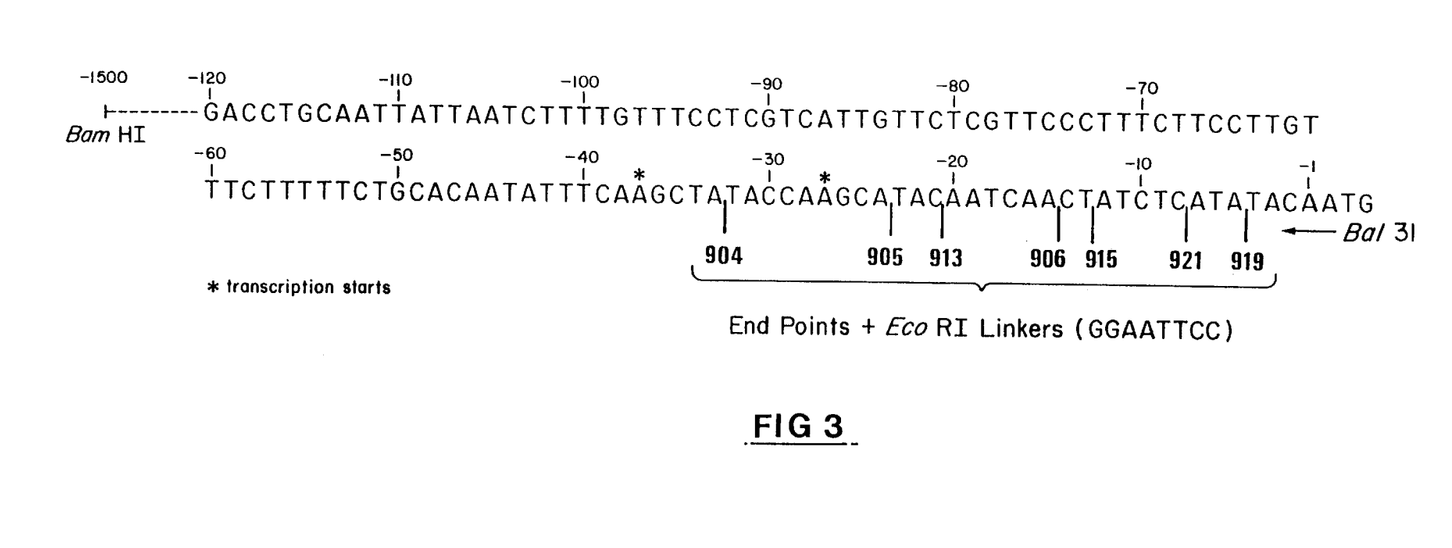
FIG. 3 illustrates the coding strand sequence and end points (904, 906, etc.) of a series of yeast promoter fragments made by digestion with the exonuclease Bal 31; and attachment of EcoRI molecular recombinational linkers.

FIG. 3 shows the DNA sequences of the transcribed strand of 8 of the resulting, variously sized and numbered promoter fragments. The numbered lines show where the right end of the fragment ends and where the EcoRI linker sequence begins.

The ends of fragments 904 and 906 were exactly determined by sequencing. The EcoRI sticky ends of these fragments were labelled with Klenow DNA polymerase using $\alpha$-$^{32}$P-dATP. A sequencing gel was used to read from the A's into the linker through the junction. The other 6 fragment ends were approximated to within about 1–2 base pairs by labelling as above, cutting with AluI, followed by sizing on the same denaturing gel.

Figure 4:
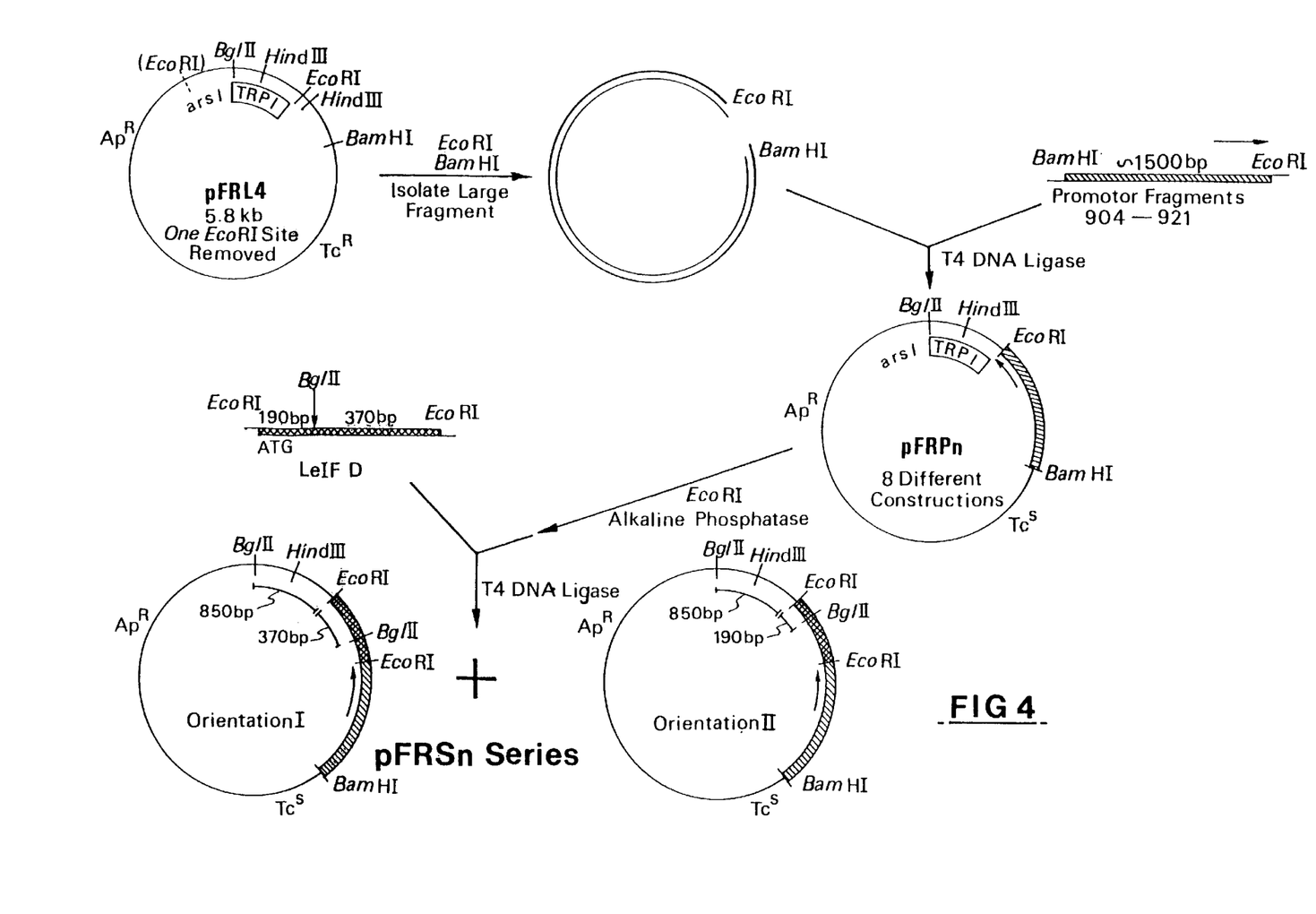
FIG. 4 schematically illustrates the insertion of yeast promoter fragments into the transfer vector of FIG. 1 and subsequent insertion (in two orientations) of a structural gene encoding human leukocyte interferon D.

Construction of Plasmids that Express Biologically Active Leukocyte Interferon D in Yeast In order to optimize for successful expression of LeIF D in yeast, eight different promoter fragments (FIG. 3) were ligated into the pFRL4 vector as shown in FIG. 4.

The vector was designed to have ADH promoter transcription in the same direction as TRP1 gene transcription (31). Since the LeIF D gene was to be inserted in the EcoRI site and was not known to contain proper 3' termination and processing sequences for yeast-recognition, the TRP1 gene flanking sequence was aligned to perform these functions.

The resulting pFRPn series (where n is the promoter fragment number) was obtained as shown. The preferred embodiment of these, pFRP6 in a transformant strain of $E.$ $coli$ 294, has been deposited in the American Type Culture Collection (ATCC no. 31814). These vectors were cut with EcoRI, alkaline phosphatase treated (to avoid premature recircularization), and ligated with the EcoRI LeIF D gene fragment. The ATG of this gene immediately follows the C of the EcoRI linker (GAATTCATG) as shown (FIG. 4).

Ampicillin resistant transformants of $E.$ $coli$ K-12 strain 294 were screened to find plasmids containing both orientations of the LeIF D fragment (pFRSn series—n refers to screening number). Orientations were determined by agarose gel electrophoresis using BglII digestion which cuts both in the vector and in the LeIF D gene as shown.

Three of the plasmids demonstrated unpredicted restriction patterns. pFRS7 and pFRS35 have an extra BglII fragment at 560 bp. This results from having two fragments of LeIF D in line with ADH transcription. pFRS16 has no proper orientation fragment but has a 1700 bp fragment which apparently resulted from the ligation of two vector fragments together (two TRP1 containing "tails" together) with one LeIF D fragment in between two "heads" containing ADH promoter fragments. Thus in this ligation product the interferon gene is in the proper orientation for expression by one of the ADH promoter fragments.

Evidence for Leukocyte Interferon D Expression in Yeast

First the $E.$ $coli$ 294 strains containing the various plasmids (pFRSn) were grown and extracts prepared (see Methods). No interferon activity was observed in the extracts using the cytopathic effect Inhibition assay (see Methods). However, when plasmids were purified and used for yeast transformations by selection of TRP+ phenotype using yeast RH218 (trp1 mutation), all plasmids with orientation I produced interferon activity in yeast while no plasmids with orientation II produced interferon.

Table 1 shows the results of interferon assays which measure antiviral activity effects on VSV virus challenge of MDBK tissue culture cells (see Methods). Seven of the promoter fragments definitely express the LeIF D gene when the gene is in the proper orientation (I). This is demonstrated by comparing units/(ml of extract) for the orientation I plasmids with the orientation II plasmids. All orientation II plasmids expressed <1900 units/(ml of extract), a value 1 to 4 percent of the values for orientation I plasmids (actually background values are probably much lower than this since the 1900 value is a function of the assay procedure).

suggests that the DNA sequence in this region is relatively unimportant in transcription and translation. These results also suggest that precise spacing between the promoter and the ATG may be relatively unimportant for expression in yeast.

In addition, Table 1 shows molecules/cell values which are very much higher than the 10,000 molecules/cell observed for interferon D expression in E. coli. Interferon D expression in E. coli on a high copy plasmid with a strong promoter (trp promoter) (32). Assessment of this extreme difference (up to 18 fold) in molecules per cell should recognize that the yeast cell volume is probably 2 orders of magnitude higher than that of E. coli; however, the amount of expression from only 1–2 copies of the yeast plasmid versus the high copy number of plasmids producing interferon in E. coli is dramatic.

Comparison of the Size of Interferon Produced in Yeast versus E. coli

Since the interferon gene uses its own ATG-initiation codon and since the alcohol dehydrogenase ATG has been

| Orientation | ADH promoter fragment | Plasmid | Units[a]/ml of extract | Units/l of cells × $10^{-6}$ | Units[b]/l of cells at Abs = 1 × $10^{-6}$ | Cells[c]/l of culture × $10^{-10}$ | Pct.[c] of cells with plasmid | Units/cell containing plasmid × $10^4$ | Molecules[d]/cell containing plasmid |
|---|---|---|---|---|---|---|---|---|---|
| I | 904 | pFRS3 | 47,000 | 1.4 | 1.2 | 2.1 | 19 | 3.5 | 53,000 |
| I | 905 | pFRS7 | 47,000 | 1.4 | 0.54 | 3.4 | 30 | 1.4 | 21,000 |
| I | 913 | pFRS16 | 187,500 | 5.6 | 2.0 | 5.1 | 32 | 3.4 | 51,000 |
| I | 906 | pFRS12 | 125,000 | 3.8 | 1.8 | 2.7 | 19 | 7.4 | 110,000 |
| I | 906 | pFRS36 | 187,500 | 5.6 | 2.3 | 3.0 | 16 | 12 | 180,000 |
| I | 915 | pFRS23 | 125,000 | 2.1 | 0.81 | 3.6 | 21 | 2.8 | 42,000 |
| I | 921 | pFRS35 | 250,000 | 7.5 | 2.8 | 4.5 | 18 | 9.2 | 140,000 |
| I | 919 | pFRS34 | 93,750 | 2.8 | 1.4 | 2.2 | 17 | 7.6 | 110,000 |
| II | 904 | pFRS2 | <1900 | | | | 22 | | |
| II | 905 | pFRS6 | " | | | | 23 | | |
| II | 913 | pFRS17 | " | | | | 36 | | |
| II | 906 | pFRS11 | " | | | | 13 | | |
| II | 915 | pFRS22 | " | | | | 46 | | |
| II | 921 | pFRS26 | – | | | | 25 | | |
| II | 919 | pFRS33 | " | | | | 31 | | |

[a]Yeast cells were grown in 5 ml of YNB + CAA (Trp+ selection) to an absorbance (Abs) of 1.2 to 2.8 at 660 mμ and spheroplasted with zymolyase as described in Methods. The final pellet was resuspended in 0.15 ml of 7 M guanidine HCl and 1 mM PMSF. The extracts were assayed using 1/100 or 1/1000 dilutions in dilution buffer using an VSV virus challenge of MDBK cells (see Methods).
[b]Units/liter of cells at $Abs_{660} = 1 \times 10^{-6}$ is a normalization since different cultures were stopped between 1.2 to 2.8 $Abs_{660}$.
[c]The number of yeast cells per culture was determined by dilution and plating on YNB + CAA + tryptophan (50 μg/ml) plates. To find out how many cells have plasmid (Trp+ complementation) cultures were also plated on YNB + CAA (without tryptophan). Thus percentage of cells containing plasmid was determined.
[d]Molecules/(cell containing plasmid) was calculated assuming purified leukocyte interferon D has a specific activity of 2 × $10^8$ units/mg (27) in the same assay and a molecular weight of 20,000 g/mole.

Since ars1 (chromosomal origin of replication)-containing plasmids have previously been shown to be unstable and lost in a high percentage of the cells even under selective maintenance pressure (24, 25), the percent of cells containing the plasmid at the time of extract preparation was measured. This was done by plating diluted cultures on plates with and without tryptophan. The results of this demonstrate that the plasmid is somewhat unstable in yeast (though not in bacteria), but can be maintained by growth under selective pressure. These results also are evidence for the presence of the plasmid, since RH218 (trp1) yeast do not grow on plates without tryptophan and since a revertant to TRP+ would plate with equal efficiency on plates with and without tryptophan. Furthermore, the percentages of cells containing plasmid are similar comparing yeast with orientation I and II plasmids. This suggests that the production of interferon in the yeast cell does not result in increased instability of the plasmid due to interferon toxicity to the cell.

The fact that all the promoter fragments express interferon when up to 32 bp are removed upstream from the ATG removed in the construction, one would expect to find that the interferon expressed in yeast is the same size as the interferon in E. coli (32). SDS-polyacrylamide gel electrophoresis was accordingly done on an E. coli extract containing interferon D versus a yeast extract containing interferon D. After running the gel, two lanes containing yeast extract versus E. coli extract were simultaneously sliced. The slices were put into assay dilution buffer and left at 4° C. for 3 days. Interferon assays were then performed to compare sizes of the peptides. Both appear to be about 20,000 daltons, the size expected for interferon D. However, there does appear to be a slight difference in the molecular weights, with yeast interferon D being about 7 percent larger, possibly owing to glycosylation. Despite the size difference, the products of yeast expression exhibited interferon activity (Table 1).

The preceding data clearly demonstrates that a yeast 5'-flanking DNA sequence, without the translation start signal of the structural gene, can efficiently promote the expression of an inserted mammalian or other structural gene for a biocompetent polypeptide, and do so without the aid of selective pressure for the product of expression (i.e., the expression product is not required for cell growth).

The availability of yeast promoter-containing plasmids (pFRPn series) having both yeast and bacterial phenotypical genes and origins of replication, and a site downstream from the promoter convenient for the insertion of translation start- and stop-bearing structural genes permits the creation of DNA expression vectors for a wide variety of polypeptides. Thus, into such a site may be inserted, for example, structural genes for both normal (5) and hybrid (6) human leukocyte interferons, fibroblast interferon (7), somatostatin or the A or B chains of human insulin (1), human proinsulin (2), thymosin alpha 1 (3), human growth hormone (4) and, indeed, virtually any other biocompetent polypeptide.

Following expression, product may be extracted and purified as in the case of bacterial expression, mutatis mutandis.

It will be appreciated that the invention is not limited in its application to the particular expression vector exemplified above. For example, use of the so-called two micron origin of replication would provide additional stability, making unnecessary resort to selective pressure for maintenance of the plasmid in the yeast cell, particularly if the host strain is [CIR+], i.e., contains normal two micron plasmid (33). Such an expression vector would be stable in yeast in the rich medium ordinarily best for large scale fermentations. At the same time, use of the two micron origin of replication could significantly increase plasmid copy number in each cell.

Stability of the expression vector in yeast may also be enhanced by inclusion within the plasmid of a yeast centromere (34), an element involved in maintenance of the yeast chromosome. The resulting plasmid will behave as a minichromosome, such that selective pressure will not be required during growth or maintenance of the plasmid. As many as 17 different yeast centromeres have been identified to the present date.

Transcription terminators other than that present on the TRP1 gene may be employed, e.g., other 3'-flanking sequences from yeast such as the 3'-flanking sequence contained on a Hinc II-BamH1 fragment of the ADH 1 gene.

Optimization may also result from alteration of the sequence between the yeast promoter fragment and the inserted gene fragment. Thus, an A (adenine base) is found at position −3 (the third base before the translation start signal) of all twenty different mRNA-coding yeast genes heretofore sequenced. A variety of means (eg., use of linkers) for including such an element in the plasmids of the invention will appear to those skilled in the art.

Of course, promoters other than the ADH promoter exemplified above may be employed in variants of the invention. For example, the promoter of the yeast 3-phosphoglycerate kinase gene may be employed, doubtless increasing expression levels significantly over those observed for the ADH system. Again, one or more of the promoters for yeast glyceraldehyde-3-phosphate dehydrogenase may be employed. This system is nonfunctional in the absence of glucose, but induced 200-fold in its presence, and could accordingly be employed for fine control of expression.

From the foregoing, it will be apparent that the invention provides new means for the expression of valuable polypeptides. In particular instances, efficiency of expression relative to that in recombinant bacteria may result from the different codon usage patterns as between yeast and bacteria, such that eukaryotic genes may be better expressed in yeast.

The yeast expression systems of the invention may also provide advantage in the glycosylation of biocompetent polypeptides, an ability bacteria lack. The glycosylation system of yeast is very similar to that of higher eukaryotes, and glycosylation may prove to have profound effects on the functions of proteins.

As will be apparent to those skilled in the art in the light of the foregoing discussion, the invention is not to be limited to the preferred embodiments thereof exemplified above, but rather only to the lawful scope of the appended claims.

The contributions of certain of the coinventors hereof arose in the course of work funded in part by the United States Department of Health and Human Services.

BIBLIOGRAPHY

1. U.S. patent application Ser. No. 90,980 filed Nov. 5, 1979 by A. Riggs, assignee Genentech, Inc.
2. U.S. patent application Ser. No. 222,044, Atty. Dkt. No. 1980/109, filed Jan. 2, 1981 by D. Goeddel et al., assignee Genentech, Inc.
3. U.S. patent application Ser. No. 125,685, filed Feb. 28, 1980 by Crea et al., assignee Genentech, Inc.
4. U.S. patent application Ser. No. 55126, filed Jul. 5, 1979 by D. Goeddel et al., assignee Genentech, Inc.
5. U.S. patent application Ser. No. 205,578, filed Nov. 10, 1980 by D. Goeddel et al., assignees Genentech, Inc. and Hoffmann-La Roche, Inc.
6. U.S. patent application Atty. Dkt. No. 100/42, filed Feb. 23, 1981 by D. Goeddel et al., assignee Genentech, Inc.
7. U.S. patent application Ser. No. 190,799, filed Sep. 25, 1980 by D. Goeddel, assignee Genentech, Inc.
8. Shine et al. *Nature* 285, 456–461 (1980).
9. Beggs, J. D., van den Berg, J., van Ooyen, A., and Weissmann, C. *Nature* 283, 835–840 (1980).
10. Henikoff, S., Tatchell, K., Hall, B. D. and Nasmyth, K. A. *Nature* 289, 33–37 (1981).
11.
12. Carbon, J., Clarke, L., Chinault, C., Ratzkin, B., and Walz, A. (1978) in *Biochemistry and Genetics of Yeast* (Bacila, M., Horecker, B. L., and Stoppani, A. O. M., eds) pp. 425–443, Academic Press, New York.
13. Clarke, L. and Carbon, J. *Cell* 9, 91–99 (1976).
14. Davis, R. W., Thomas, M., Cameron, J., St. John, T. P., Scherer, S., and Padgett, R. A. *Methods In Enzymology*, Vol. 65, Part 1, p. 404–411.
15. Clark, L. and Carbon, J. *PNAS* 72, 4361–4365 (1975).
16. Hsiao, C.-L. and Carbon, J., *Proc. Natl. Acad. Sci.* USA 76, 3829–3833 (1979).
17. Birnboim, H. C., and Doly, *J. Nucleic Acids Res.* 7, 1513–1523 (1979).
18. Hitzeman, R. A., Clarke, L. and Carbon, J. *Journal of Biological Chemistry* 255, 12073–12080 (1980).
19. Backman, K., Ptashne, M., and Gilbert, W., *Proc. Natl. Acad. Sci.* USA 73, 4174–4178 (1976).
20. Miozzari, G., Neideiberger, P., and Hutter, R. *Journal of Bacteriology* 134, 48–59/(1978).
21. Faye, G., Leung, D. W., Tachell, K., Hall, B. D., and Smith, M. *Proc. Natl. Acad. Sci.* USA, in press (1981).
22. Miller, J. H. *Experiments in Molecular Genetics*, pp. 431–433, Cold Spring Harbor Laboratory, Cold Spring Harbor, N.Y.
23. Maxam, A. M., and Gilbert, W. *Methods in Enzymol.* 65, 490–565 (1980).
24. Stinchcomb, D. T., Struhl, K., and Davis, R. W. *Nature* 282, 39–43 (1979).
25. Kingsman, A. J., Clarke, L., Mortimer, R., and Carbon, J. *Gene* 7, 141–153 (1979).

26. Tschumper, G., and Carbon, J. *Gene* 10, (1980).
27. Stewart, W. E. II *The Interferon System* (Springer, New York, 1979).
28. DeMoss, J. A. *Biochem. Biophys. Res. Commun.* 18, 850–857 (1965).
29. Bolivar, F., Rodriguez, R. L., Green, P. Y., Betlach, M. C., Heyneker, H. L., Boyer, H. W., Crosa, Y. H., and Falkow, S. *Gene* 2, 95–113 (1977).
30. Williamson, V. M., Bennetzen, J., Young, E. T., Nasmyth, K., and Hall, B. D. *Nature* 283, 214–216 (1980).
31. Tschumper, G., and Carbon, J. *Gene (Amst.)* 10, 157–166 (1980).
32. Goeddel, D. V. et al. *Nature* 287, 411–416 (1980).
33. Beggs, J. D. *Nature* 275, 104–109 (1978).
34. Clarke, L., and Carbon, J. *Proc. Natl. Acad. Sci. USA* 77, 2173–2177 (1980).

We claim:

1. A process of forming a transformant of a yeast strain capable of expressing a polypeptide ordinarily exogenous to yeast, comprising transforming said yeast strain with a DNA transfer vector that comprises:
    (a) bacterial and yeast origins of replication and genes for phenotypic selection of both bacterial and yeast moieties transformed with said vector;
    (b) a DNA fragment comprising a structural gene encoding said polypeptide;
    (c) a yeast promoter genetically distinct from said structural gene obtained front the DNA sequence 5' flanking the start signal of a yeast structural gene; and
    (d) translation start and stop signals for said structural gene encoding said polypeptide that are positioned so that said structural gene encoding said polypeptide is under the control of said promoter while maintaining said origins of replications and genes for phenotypic selection.

2. The process of claim 1, wherein the vector further comprises a transcription terminator located between the 3' end of a coding strand of said structural gene encoding said polypeptide and said origins of replication.

3. The process of claim 1, wherein the DNA fragment comprising said structural gene further comprises a translation start signal and a translation stop signal.

4. The process of claim 1, wherein the gene for phenotypic selection of bacteria encodes a polypeptide that confers antibiotic-resistance and wherein the gene for phenotypic selection of yeast encodes a polypeptide that complements a mutation carried by the yeast strain to be transformed.

5. The process of claim 4, wherein the yeast strain is *Saccharomyces cerevisiae*.

6. The process of claim 5, wherein the yeast strain is strain RH 218.

7. The process of claim 1, wherein the amino acid sequence of said polypeptide is selected to correspond to the amino acid sequence of a polypeptide selected from the group consisting of the normal and hybrid human interferons, human proinsulin, the A and B chains of human insulin, human growth hormone, somatostatin, and thymosin alpha 1.

8. The process of claim 1, wherein the polypeptide is the A or B chain of human insulin.

9. The process of claim 1, wherein the yeast promoter includes a transcription start site of the yeast structural gene.

10. A process of producing a polypeptide comprising culturing a yeast strain transformed by the process of claim 1, and recovering said polypeptide.

11. The process of claim 10, wherein the amino acid sequence of said polypeptide is an intermediate from which the A and B chains of human insulin can be obtained by cleavage away of superfluous amino acids.

12. A DNA expression vector, capable in a transformant strain of yeast of expressing a polypeptide ordinarily exogenous to yeast, said vector comprising bacterial and yeast origins of replication and a yeast promoter from the DNA sequence 5' flanking the start signal of a yeast structural gene, said yeast promoter being capable of directing the expression of a gene encoding said polypeptide.

13. The DNA expression vector of claim 12, which further comprises a gene encoding a polypeptide under the control of the yeast promoter.

14. The DNA expression vector of claim 13, wherein the promoter is from within the 1500 bp DNA sequence 5' flanking the start signal of a yeast structural gene, the promoter is resected free of the yeast structural gene and the start signal of the yeast structural gene, and the gene encoding the polypeptide is located at the endpoint of the resection.

15. The DNA expression vector of claim 13, which further comprises a transcription terminator following the gene encoding the polypeptide in the 3' direction in which the gene is transcribed.

16. The DNA expression vector of claim 15, wherein the polypeptide is a mammalian polypeptide.

17. The DNA expression vector of claim 13, which further comprises a gene encoding a polypeptide for phenotypic selection of a yeast transformant.

18. The DNA expression vector of claim 17, which further comprises a gene for encoding a polypeptide for phenotypic selection in bacteria.

19. The DNA expression vector of claim 18, wherein the gene encoding the polypeptide for phenotypic selection in bacteria comprises a gene encoding a polypeptide that confers antibiotic resistance and the gene encoding the polypeptide for phenotypic selection of the yeast transformant comprises a gene encoding a polypeptide that complements a mutation carried by the yeast strain to be transformed with the expression vector.

20. The DNA expression vector of claim 13, wherein the polypeptide comprises the amino acid sequence of a polypeptide having the activity of a polypeptide selected from the group consisting of normal and hybrid human interferons, human proinsulin, the A and B chains of human insulin, human growth hormone, somatostatin, and thymosin alpha 1.

21. The DNA expression vector of claim 13, wherein the polypeptide is the A or B chain of human insulin.

22. The DNA expression vector of claim 13, wherein the polypeptide is a mammalian polypeptide.

23. The DNA expression vector of claim 13, wherein the yeast promoter comprises a promoter for the yeast 3-phosphoglycerate kinase, glyceraldehyde-3-phosphate dehydrogenase, or alcohol dehydrogenase structural genes.

24. The DNA expression vector of claim 13, wherein the promoter is a yeast alcohol dehydrogenase promoter.

25. The DNA expression vector of claim 13, wherein the origin of replication is the 2 micron yeast plasmid origin of replication.

26. The DNA expression vector of claim 13, wherein the structural gene is a yeast chromosomal gene.

27. The DNA expression vector of claim 13, wherein the yeast promoter further comprises a yeast transcription start site.

28. A process of producing a polypeptide comprising transforming a yeast strain with the DNA expression vector of claim 12, culturing the transformed yeast strain, and recovering said polypeptide.

29. A yeast strain comprising a gene encoding a polypeptide ordinarily exogenous to yeast under the control of a yeast promoter from the DNA sequence 5' flanking the start signal of a yeast structural gene.

30. The yeast strain of claim 29, wherein the yeast promoter is resected free of the yeast structural gene and the gene encoding the polypeptide is located at the endpoint of the resection.

31. The yeast strain of claim 29, wherein the polypeptide has the amino acid sequence of a polypeptide having, the activity of a polypeptide selected from the group consisting of normal and hybrid human interferons, human proinsulin, the A and B chains of human insulin, human growth hormone, somatostatin, and thymosin alpha 1.

32. The yeast strain of claim 29, wherein the polypeptide is the A or B chain of human insulin.

33. The yeast strain of claim 29, wherein the polypeptide is a mammalian polypeptide.

34. A yeast strain capable of expressing a polypeptide ordinarily exogenous to yeast produced by a process comprising transforming said yeast strain with a DNA transfer vector comprising:

(a) bacterial and yeast origins of replication and genes encoding polypeptides for phenotypic selection of both bacterial and yeast moieties transformed with said vector;

(b) a DNA fragment comprising a structural gene encoding said polypeptide;

(c) a DNA fragment comprising a yeast promoter from the DNA sequence 5' flanking the start signal of a yeast structural gene;

(d) translation start and stop signals for said structural gene encoding said polypeptide positioned such that said structural gene for said polypeptide is under the control of said yeast promoter, while maintaining said origins of replication and genes encoding polypeptides for phenotypic selection.

35. The yeast strain of claim 34, wherein said yeast promoter is resected free of said yeast structural gene and the gene encoding said polypeptide is located at the endpoint of the resection.

36. The yeast strain of claim 34, wherein said polypeptide comprises the amino acid sequence of a polypeptide having the activity of a polypeptide selected from the group consisting of normal and hybrid human interferons, human proinsulin, the A and B chains of human insulin, human growth hormone, somatostatin, and thymosin alpha 1.

37. The yeast strain of claim 34, wherein the yeast promoter further comprises a yeast transcription start site.

38. A process of producing a polypeptide comprising culturing the yeast strain of claim 34, and recovering said polypeptide.

* * * * *

UNITED STATES PATENT AND TRADEMARK OFFICE
CERTIFICATE OF CORRECTION

PATENT NO. : 5,919,651
DATED : July 6, 1999
INVENTOR(S) : R.A. Hitzeman et al.

It is certified that error appears in the above-identified patent and that said Letters Patent is hereby corrected as shown below:

Title page, item [56]

| | | | |
|---|---|---|---|
| [56] Pg. 1, col. 2 | Refs. Cited (Other Publs., #11) | "centromer- e-linked" should be hyphenated | --centromere- linked-- |
| [56] Pg. 3, col. 2 | Refs. Cited (Other Publs., #85) | "2-λm" should read --2-µm-- | |

| COLUMN | LINE | |
|---|---|---|
| 5 | 38 | "ma1" should read --mal-- |
| 5 | 47 | "yeasts" should read --yeast-- |
| 5 | 50 | "(YNB),(Difco)," should read --(YNB) (Difco),-- |
| 8 | 16 | "3000xg" should read --3000 xg-- |
| 10 | 9 | "Xhoh" should read --XhoI-- |
| 11 | 2 | "Inhibition" should read --inhibition-- |
| 11 | 20 | Directly above the table, insert: --Table 1 Interferon activity in yeast extracts-- |

UNITED STATES PATENT AND TRADEMARK OFFICE
CERTIFICATE OF CORRECTION

PATENT NO. : 5,919,651
DATED : July 6, 1999
INVENTOR(S) : R.A. Hitzeman et al.

It is certified that error appears in the above-identified patent and that said Letters Patent is hereby corrected as shown below:

| COLUMN | LINE | |
|---|---|---|
| 11 (Table 1, | 37 | "-" should read --"-- |
| 14 | 49 | "Doly, *J.*" should read --Doly, J.-- |
| 15 (Claim 1, | 28 line 11) | "front" should read --from-- |
| 17 (Claim 31, | 10 line 2) | After "having" delete "," |

Signed and Sealed this

First Day of August, 2000

Attest:

Q. TODD DICKINSON

*Attesting Officer*    *Director of Patents and Trademarks*